(12) United States Patent
Stauch

(10) Patent No.: US 9,636,153 B2
(45) Date of Patent: May 2, 2017

(54) MEDULLARY PIN

(71) Applicant: WITTENSTEIN AG, Igersheim (DE)

(72) Inventor: Roman Stauch, Assamstadt (DE)

(73) Assignee: Wittenstein SE, Igersheim (DE)

( * ) Notice: Subject to any disclaimer, the term of this patent is extended or adjusted under 35 U.S.C. 154(b) by 0 days.

(21) Appl. No.: 14/833,411

(22) Filed: Aug. 24, 2015

(65) Prior Publication Data

US 2016/0058483 A1 Mar. 3, 2016

(30) Foreign Application Priority Data

Sep. 1, 2014 (DE) .................. 10 2014 112 573

(51) Int. Cl.
*A61B 17/72* (2006.01)
*A61B 17/00* (2006.01)
*A61B 17/68* (2006.01)

(52) U.S. Cl.
CPC ...... *A61B 17/7216* (2013.01); *A61B 17/7241* (2013.01); *A61B 2017/00017* (2013.01); *A61B 2017/00991* (2013.01); *A61B 2017/681* (2013.01)

(58) Field of Classification Search
CPC .......... A61B 2017/681; A61B 17/7216; A61B 17/7225; A61B 17/7241; A61B 17/72
See application file for complete search history.

(56) References Cited

U.S. PATENT DOCUMENTS 4,875,475 A * 10/1989 Comte ............... A61B 17/7225
606/64
5,074,882 A 12/1991 Grammont et al.
5,263,955 A * 11/1993 Baumgart .......... A61B 17/7216
606/62

(Continued)

FOREIGN PATENT DOCUMENTS

BE WO 2012003555 A1 * 1/2012 ......... A61B 17/7216
DE 19708279 A1 9/1998
(Continued)

OTHER PUBLICATIONS

European Search Report for EP 15 183 181.5 dated Jan. 8, 2016.

*Primary Examiner* — Lynnsy Summitt
(74) *Attorney, Agent, or Firm* — Bachman & LaPointe, PC

(57) ABSTRACT

Medullary pin (1) for a distraction with segment transport and subsequent lengthening of a tubular bone, wherein the medullary pin (1) comprises: an at least partly hollow body (3) extending in an axial direction of the medullary pin (1), a locking means for locking the body (3) in a first end fragment (5) of the tubular bone, a first inner part (7), which is arranged displaceably in the axial direction inside the body (3) and comprises a first fixation means for the fixation of a middle fragment (15) of the tubular bone, a second inner part (17), which is arranged displaceably in the axial direction inside the body and comprises a second fixation means for the fixation of a second end fragment (25) of the tubular bone, and a drive unit (40) for the axial displacement of the (Continued)

first inner part (7) relative to the second inner part (17), wherein the drive unit (40) is arranged inside the body (3) between the first fixation means of the first inner part (7) and the second fixation means of the second inner part (17).

11 Claims, 1 Drawing Sheet

(56) References Cited

U.S. PATENT DOCUMENTS

| | | | | |
|---|---|---|---|---|
| 5,626,579 | A * | 5/1997 | Muschler | A61B 17/7216 606/60 |
| 5,976,138 | A | 11/1999 | Baumgart et al. | |
| 6,056,755 | A * | 5/2000 | Horas | A61B 17/7216 606/62 |
| 7,063,706 | B2 | 6/2006 | Wittenstein | |
| 7,666,184 | B2 * | 2/2010 | Stauch | A61B 17/7216 606/63 |
| 7,753,915 | B1 * | 7/2010 | Eksler | A61B 17/663 606/105 |
| 8,043,299 | B2 * | 10/2011 | Conway | A61B 17/7216 606/105 |
| 8,157,802 | B2 * | 4/2012 | Elghazaly | A61B 17/744 606/64 |
| 8,449,543 | B2 * | 5/2013 | Pool | A61B 17/1725 606/105 |
| 8,632,544 | B2 * | 1/2014 | Haaja | A61B 17/7216 606/63 |
| 8,632,548 | B2 * | 1/2014 | Soubeiran | A61B 17/025 606/90 |
| 8,715,282 | B2 * | 5/2014 | Pool | A61B 17/7216 606/57 |
| 8,915,915 | B2 * | 12/2014 | Harrison | A61B 17/7016 606/60 |
| 9,044,281 | B2 * | 6/2015 | Pool | A61B 17/84 |
| 9,113,967 | B2 * | 8/2015 | Soubeiran | A61B 17/7014 |
| 9,138,266 | B2 * | 9/2015 | Stauch | A61B 17/7216 |
| 9,179,938 | B2 * | 11/2015 | Pool | A61B 17/7016 |
| 9,308,089 | B2 * | 4/2016 | Vicatos | A61B 17/7216 |
| 2006/0293683 | A1 | 12/2006 | Stauch | |
| 2008/0221577 | A1 * | 9/2008 | Elghazaly | A61B 17/744 606/64 |
| 2011/0054473 | A1 * | 3/2011 | Brigido | A61B 17/1725 606/62 |
| 2011/0196435 | A1 * | 8/2011 | Forsell | A61B 17/68 606/86 R |
| 2011/0238126 | A1 * | 9/2011 | Soubeiran | A61B 17/7216 606/86 R |
| 2012/0130370 | A1 * | 5/2012 | Kinmon | A61B 17/7241 606/62 |
| 2012/0209265 | A1 * | 8/2012 | Pool | A61B 17/7216 606/55 |
| 2013/0012943 | A1 * | 1/2013 | Prager | A61B 17/72 606/67 |
| 2013/0072932 | A1 | 3/2013 | Stauch | |
| 2013/0165733 | A1 * | 6/2013 | Rogachefsky | A61N 2/008 600/12 |
| 2014/0052134 | A1 * | 2/2014 | Orisek | A61B 17/7216 606/63 |
| 2014/0296918 | A1 * | 10/2014 | Fening | A61B 17/7016 606/258 |
| 2016/0183994 | A1 * | 6/2016 | Quach | A61B 17/8866 606/90 |

FOREIGN PATENT DOCUMENTS

| | | | | |
|---|---|---|---|---|
| DE | WO 2004091414 | A1 * | 10/2004 | A61B 17/7216 |
| DE | 10317776 | A1 | 11/2004 | |
| DE | 102011053638 | A1 | 3/2013 | |
| EP | 2570092 | A2 | 3/2013 | |
| WO | 9522292 | A1 | 8/1995 | |
| WO | 2009152270 | A1 | 12/2009 | |
| WO | 2011116158 | A2 | 9/2011 | |

* cited by examiner

MEDULLARY PIN

BACKGROUND OF THE INVENTION

The invention concerns a medullary pin for a distraction and subsequent lengthening of a tubular bone with segment transport.

Medullary pins are known from the prior art, such as DE 10 2011 053 638 A1, which make possible a distraction of long tubular bones with segment transport. Two bone fragments, a distal end fragment and a proximal end fragment, are displaced relative to each other by means of a medullary pin. Furthermore, a middle bone fragment exists in applications with segment transport, also being known as the segment and likewise being part of the fractured bone. At a contact site between one of the end bone fragments and the middle fragment, bone is supposed to grow back. This is accomplished by selecting the rate of advance of the middle fragment for the distraction to be sufficiently small.

Such displacements enable a treatment of major bone defects of more than 3 cm, for example, such as may occur as a result of diseases or violent impact. Major bone defects may also occur in operations due to bone tumors, which can be treated with a medullary pin with segment displacement depending on the severity of the disease.

One challenge in the case of medullary pins with transport of a middle fragment is principally the fixation of the ends of the medullary pin in the proximal bone fragment and the distal bone fragment. Especially in the case of short fragments at the ends of the bone, the medullary pins known from the prior art can be hard to anchor.

The problem of the invention is to indicate a medullary pin, wherein systems or medullary pins known from the prior art should be improved, in particular, the drawbacks of the prior art should be mitigated or eliminated. Medullary pins are desirable which require the least possible surgical expense or which enable a dependable fixation even in short bone end fragments.

SUMMARY OF THE INVENTION

The problem is solved with a medullary pin according to the present invention.

One aspect of the invention involves a medullary pin for a distraction and subsequent lengthening of a tubular bone with middle fragment transport, wherein the medullary pin comprises: an at least partly hollow body extending in an axial direction of the medullary pin, a locking means for locking the body in a first end fragment of the tubular bone, a first inner part which is arranged displaceably in the axial direction inside the body and comprises a first fixation means for the fixation of a middle fragment of the tubular bone, a second inner part, which is arranged displaceably in the axial direction inside the body and comprises a second fixation means for the fixation of a second end segment of the tubular bone, and a drive unit for the axial displacement of the first inner part relative to the second inner part, wherein the drive unit is arranged inside the body between the first fixation means of the first inner part and the second fixation means of the second inner part.

Sample embodiments of medullary pins have a hollow body extending in the axial direction of the medullary pin. The hollow body makes it possible to accommodate displaceable inner parts.

In typical embodiments, the drive unit is integrated with the second inner part. In other typical embodiments the drive unit is integrated with the first inner part. The term "integrated" means in particular that the drive unit is integrated in the inner part. An integrated design of the drive unit with the inner part can be used to integrate the drive unit in one of the inner parts. The drive unit in typical embodiments has a floating design. This means in particular that the drive unit is displaceable in the axial direction. Typically, the drive unit is displaceable with the inner part in which it is integrated. In other embodiments, the drive unit is a part separate from the inner parts. For example, the drive unit lies with one side against one of the inner parts without fastening or with a fixation. Typically, a spindle is arranged on one side of the drive unit, which interacts with an internal thread in one of the inner parts. In this way, the drive unit can move the two inner parts away from each other. In the case of an integral design or a fixation to one inner part, the drive unit can also be used to move the inner parts toward each other. A second drive unit is provided in some embodiments. Two drive units can be used to move the inner parts to certain positions independently of each other.

In typical embodiments, the at least one drive unit is arranged between the fixation means of the inner parts. In this way, the second inner part can be used also to be joined to short end fragments. In the case of an integral design of the drive unit in one of the inner parts, the drive unit is arranged at the side facing the other inner part.

Typically, a first pair of axially extending oblong holes opposite each other is arranged in the middle region of the body. This allows for the passage of at least one radially oriented fixation bolt or a screw for the fastening of a middle fragment. The middle fragment can also be called the transport segment. The term "middle region" refers here to a region not situated at one end of the body. In particular, "middle region" does not refer only to the geometrical center of the body. Instead, the "middle region" extends across a larger region than only the exact geometrical center. In typical embodiments, a second pair of axially extending oblong holes opposite each other is arranged in the second end region of the body. In this way, one or more fixation bolts can be led through the body and through the second inner part in the radial direction for the fixation of a second end fragment, in order to join the second end fragment to the second inner part. The arrangement of oblong holes makes it possible to fix a bone fragment, i.e., a middle fragment or an end fragment, with one or more fixation bolts. The middle fragment is typically a part of the bone which is situated between a first end fragment and a second end fragment. In some embodiments, the first bone fragment can be a proximal bone fragment or a distal bone fragment. Accordingly, the second end fragment is then a distal bone fragment or in the other case a proximal bone fragment.

Exemplary medullary pins are especially suitable for treatment of fractures or other injuries of long tubular bones, while other injuries might be bone loss due to tumors, necessary resectioning, or violent impact, for example. Bones which can be treated with typical medullary pins are the thigh bone (femur) and shin bone (tibia), but the upper arm bone (humerus), ulna, radius and fibula can also be treated. Typical medullary pins specified here are also especially suitable for small stature or underaged patients, since the design of exemplary medullary pins of the invention requires a comparatively short length of the bone fragments for the locking.

Typical medullary pins of the invention have a locking means for locking the body in the first end fragment of the tubular bone. In this way, the body can be fixed to a first end fragment of the tubular bone in all directions and all rotations. The body is thus fixed to the bone fragment in all degrees of freedom. Typically, the locking means is arranged in a first end region of the body. This enables a fixation of an end fragment. The locking means of the body comprises in some embodiments radially oriented boreholes, such as at least two through or blind boreholes typically arranged with a rotation relative to each other about the longitudinal axis of the medullary pin. The locking means in some embodiments comprises bolts or screws, which can be received in the boreholes. The screws or bolts enable an anchoring of the body in the first end fragment.

In typical embodiments, the locking means comprises boreholes or locking bolts which are oriented exclusively radially. Some embodiments have only boreholes, which make an angle, especially an angle of at least 30°, at least 50°, or at least 80° with the longitudinal axis of the medullary pin. Radially oriented bolts offer a good purchase in bone. In other embodiments, bolts or screws are provided in addition, oriented longitudinally to the medullary pin, to stabilize the locking.

As the drive unit, an electric motor with gearing is typically provided. Typical gearing is planetary gearing; other embodiments comprise planetary roller gearing. For the power supply and control of the drive unit, a control unit is typically provided, which can be supplied with energy or control signals via an antenna wirelessly from outside the body of the person in whom the medullary pin is implanted. In some embodiments, the control unit is able to wirelessly relay or send metered data, such as a force required for the displacement or a displacement distance already covered. Basically, the wording that the "drive unit is arranged inside the body" means that all parts of the drive unit, i.e., stator and rotor of an electric machine, are arranged inside the body. Typically, the drive unit is entirely accommodated in the body. In other embodiments, the drive unit is only partly accommodated in the body. Typical drive units of other embodiments comprise a magnetic drive unit, in which the drive unit has magnets inside the body, which are moved or activated by a magnetic field generated outside the medullary pin and optionally also outside the patient's body. In other embodiments, the drive unit is a shape memory alloy or another drive unit, such as a piezoelectric actuator. Both piezoelectric actuators and electrical machines or also shape memory alloys are typically supplied with energy by an electrical connection.

In typical embodiments, the first inner part is arranged in a middle region of the body. This enables a fastening or fixation of a middle fragment to the first inner part. Typically, the second inner part is arranged in a second end region of the body. This enables a fixation or fastening of the second inner part to a second end fragment.

Typically, the first inner part and the second inner part have a cylindrical shape. In typical embodiments, the diameter of the first inner part and the second inner part is identical. In preferred embodiments, the inner parts have no molded shapes, i.e., the inner parts are formless. This offers the advantage of an easy fabrication and a certain avoidance of skewing or the like. However, it is also possible to provide lugs in order to specify the position of the inner parts in the body in addition to the fixation bolts. The term "formless" refers to the outer boundary surface of the respective inner part, in particular the first inner part usually has an internal thread. In typical embodiments, both inner parts have an outer diameter which corresponds essentially to the inner diameter of the body. Typically, the outer diameter is at most 1 mm or at most 0.5 mm smaller than the inner diameter of the hollow body.

In typical embodiments, at least one of the inner parts, optionally along with the drive unit, can rotate in the body. A guiding is accomplished solely by the radially installed fixation bolts or fixation screws and by the oblong holes. This simplifies the design. In other embodiments, at least one of the inner parts has a guide, which prevents a twisting of the inner part in the body. This can facilitate the installation.

The first inner part is typically fashioned as a sleeve, which has an internal thread for engaging with a spindle. Typically, a spindle is provided at the takeoff side of the gearing. The spindle typically constitutes a mechanical connection between the drive unit or the second inner part on the one hand and the first inner part on the other hand. In other embodiments, the second inner part is outfitted with an internal thread for a spindle, especially in embodiments in which the drive unit is integrated with the first inner part.

Typical embodiments include a bar as the first inner part, for the fixation of the bone segment. Such a bar offers the advantage of an easy design. The bar is preferably oriented transverse to the direction of a spindle of the drive unit. Thus, the bar preferably forms a single piece with both the first inner part and the fixation means, since it is anchored directly in a middle fragment. Exemplary embodiments with multiple-piece bar comprise an inner part, typically similar to a nut, and a radially projecting bar element. For this, the bar is typically provided with a recess. This recess preferably engages by form fitting with an inner part sitting on the spindle, which is designed as a threaded element with a centrally disposed internal thread. This embodiment allows a reduction in the design length or the possibility of performing larger distraction distances.

Usually, at least one of the inner parts, typically both inner parts, have at least one through opening extending in the radial direction to accommodate a fixation bolt. The through openings in some embodiments are part of the fixation means of the inner parts. In typical embodiments, at least one inner part has two or more through openings oriented in the radial direction and parallel to accommodate fixation bolts. This offers the advantage that the second end fragment and the middle fragment can be securely fixed. In other embodiments, at least one of the inner parts has precisely one radial through opening. This facilitates the fixation of a fragment during an operation.

In typical embodiments, a supply of energy to the drive unit occurs by way of an electrical connection, which is arranged inside the body. This allows an energy supply with no further damage to the bone. Typically, the electrical connection is led through the second inner part, for example, through an axial borehole of the second inner part. In this way, the electrical connection is protected against damage. In other embodiments, an energy supply is led through the first inner part.

Preferably a Herzog curvature is provided at one end of the body. This offers the possibility of also installing the medullary pin in a shin bone (tibia). Preferably, the Herzog curvature is provided at the end of the drive unit. In typical embodiments, the drive unit is arranged opposite the second inner part, that is, the first inner part lies between the second inner part and the drive unit. Preferably, the body is ideally cylindrical except for the Herzog curvature and the openings through which bolts or locking means are led through. "Ideally cylindrical" here means in particular that no other pins or lugs or oblong openings are provided on the body. In typical embodiments, the medullary pin is configured such that the Herzog curvature and the drive unit are arranged proximally. Typically, the drive unit is arranged distally, i.e., behind or beneath the Herzog curvature.

BRIEF DESCRIPTION OF THE DRAWINGS

Embodiments shall now be explained more closely with the aid of the enclosed figures, where the figures show.

DETAILED DESCRIPTION

Sample embodiments shall now be described with the aid of the figures, using the same reference numbers for the same or similar parts. At times, the same or similar parts are not explained again in conjunction with each figure.

Figure 1:
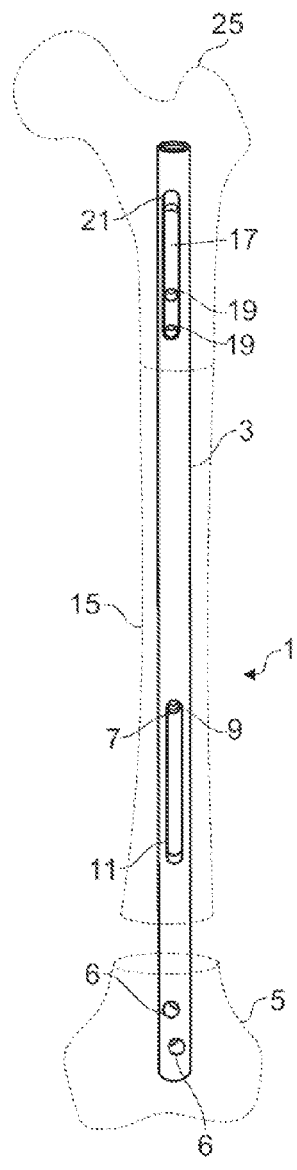
FIGS. 1 to 3, in schematic views, a medullary pin in a typical embodiment in three different operating states.
Figure 2:
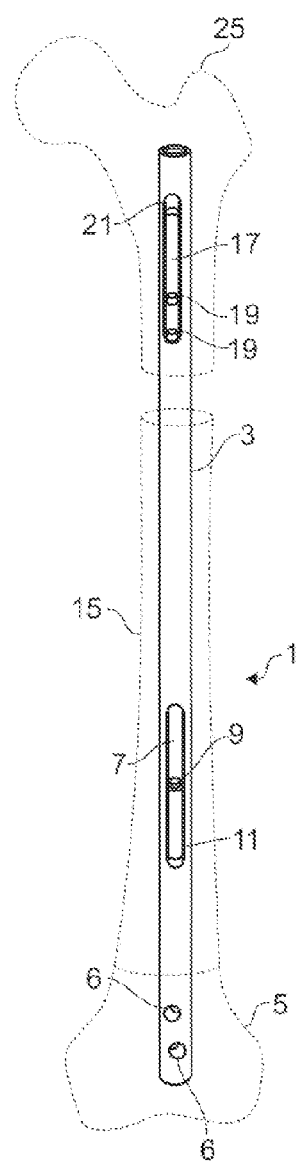
Figure 3:
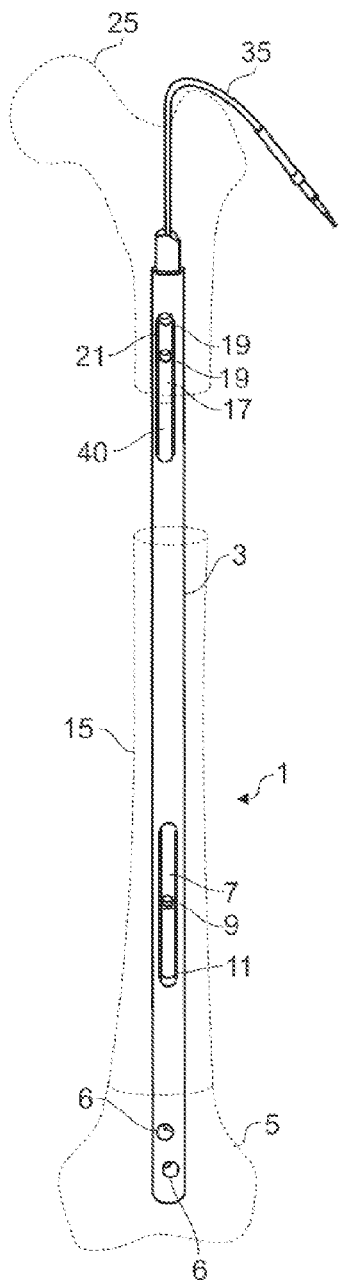

FIGS. 1 to 3 show typical embodiments of a medullary pin 1 in three different operating states. Fragments of a thigh bone are shown by broken line. These fragments are not part of the sample embodiment and serve only for illustration.

The medullary pin 1 comprises a partly hollow body 3. The body 3 is fashioned hollow throughout in the axial direction with uniform internal diameter, apart from a first end region.

Other sample embodiments of medullary pins comprise bodies having internal steps or shoulders, for example, as end stops for inner parts. In this way, displacement ranges of the inner parts can be delimited.

The body 3 has in a first end region of the body 3 locking means with which the body 3 can be locked in a first end fragment 5 of the bone. The locking means comprise two radial boreholes 6, which are arranged in the first end region of the body 3. In one use of the medullary pin 1 there are locking bolts installed in the boreholes 6, assuring a fixed connection between the first end fragment 5 and the body 3. In FIGS. 1-3, no locking bolts are shown. As the locking bolts, one can use bolts known from the prior art for the fixation of medullary pins in bones.

Essentially, the terms "radial" and "axial" pertain to the longitudinal axis of the body of the medullary pin.

In a middle region of the body 3 a first inner part 7 is accommodated, of which only a short piece can be seen in FIG. 1. The first inner part 7 is cylindrical with an outer diameter which is only slightly less than the inner diameter of the hollow body 3 in this region. The first inner part 7 has a first fixation means, which comprises a radial through opening 9, in which a fixation bolt can be installed.

Basically, the same bolts or bolts differing only in dimensions can be used for the fixation bolts of the embodiments, such as are known from the prior art for the fastening of medullary pins in bone.

In the middle region of the body 3, the body 3 has a first pair of axially oriented oblong holes 11 opposite each other. The first pair of oblong holes 11 serves to contain a passageway for a fixation bolt, which is also pushed through the through opening 9. In this way, it is possible to fix a middle fragment 15 of the bone to the first inner part 7. Moreover, in this way the inner part 7 is prevented from twisting.

A prevention of twisting by fixation bolts in the oblong holes can be advantageous in certain embodiments, especially if one of the inner parts has an internal thread, which cooperates with a spindle of a drive unit. In this way, a rotation abutment is created.

The drive unit will be explained in connection with FIG. 3, whereas the spindle and the internal thread are not depicted in FIGS. 1-3, since they lie inside the body 3 or the first inner part 7.

In a second end region, a second inner part 17 is provided, which contains additional through openings 19. The two additional through openings 19 of the second inner part 17 serve to cooperate with additional fixation bolts, which are used to fix a second end fragment 25 of the bone. In the second end region of the body 3 a second pair of oblong holes 21 is arranged, through which the additional fixation bolts can reach. The second inner part 17 is thus prevented from twisting. In this way, an abutment is created for the rotary drive unit.

An electrical connection 35 in the form of a cable is led out from the second inner part 17. Inside the inner part 18 is provided an axial borehole, which lies off center so that the axial borehole is arranged outside of the region of the radial through openings 19 of the second inner part, which are oriented centrally to the longitudinal axis.

The electrical connection 35 serves to provide current to the drive unit 40 and furthermore to control it. Moreover, a sensor signal such as that of a force sensor can be carried by the electrical connection 35, which detects a force between the first inner part 7 and the second inner part 17 in the axial direction.

In one use of the medullary pin 1, this is arranged in a bone as shown schematically in FIG. 1 and joined with locking bolts and fixation bolts to the bone fragments, i.e., the end fragments 5 and 25, as well as the middle fragment 15. In operation, the drive unit 40 pushes the two inner parts 7 and 17 away from each other, the two inner parts 7 and 17 being mounted floating with the drive unit, i.e., freely displaceable in the axial direction. The inner parts 7 and 17 can also be pulled together with the drive unit 40.

The middle fragment 15 is displaced distally in the patient's body and downward in FIGS. 1-3 by the inner parts 7 and 17 moving apart, until the middle fragment 15 abuts against the first end fragment 5 and is braced there. During this process, bone is formed once more in the gap between the middle fragment 15 and the second end fragment 25. Typical rates for the relative movement of the inner parts 7 and 17 are between 0.2 mm and 2.5 mm per day, especially between 0.5 mm and 1.5 mm per day.

By virtue of the abutment or thrusting of the middle fragment 15 against the first end fragment 5, see FIG. 2, the middle fragment 15 can grow together with the first end fragment 5, optionally assisted by a pressing action or compression. During the moving apart of the inner parts 7 and 17, bone has already grown back in the proximal gap between the second end fragment 25 and the middle fragment 15.

Once the middle fragment 15 has reached the first end fragment 5, the further moving apart of the two inner parts 7 and 17 has the effect of pushing the second end fragment 25 proximally, upward in FIGS. 1-3. This is shown schematically in FIG. 3.

With certain embodiments of the medullary pin of the invention, major bone defects can be closed up with a single operation to install the medullary pin even in the case of short lengths of the end fragments. No interim operations are needed to bring about lengthening or the like.

In FIG. 3, the second inner part 17 has been displaced so far proximally that the driving part with the drive unit 40 of the second inner part has arrived in the region of the second pair of oblong holes 21. The drive unit 40 is integrated with the second inner part 17, that is, the second inner part 17 comprises the drive unit 40. The spindle of the drive unit 40 connects the first inner part 7 to the second inner part 17 and pushes the two inner parts 7 and 17 apart upon rotation of the drive unit 40, which has a planetary gearing to step down the transmission ratio.

The electrical connection 35 is connected to a receiver, which is placed subcutaneously, in order to make possible a control and an energy supply of the medullary pin 1 via an extracorporal transmitter.

The invention is not confined to the above described sample embodiments, but instead the scope of the invention is determined by the claims. In particular, not all parts shown are necessarily features of the invention; this holds especially for the depicted human bones.

The invention claimed is:

1. A medullary pin for a distraction with segment transport and subsequent lengthening of a tubular bone, wherein the medullary pin comprises:
    an at least partly hollow body extending in an axial direction of the medullary pin,
    a locking means for locking the body in a first end fragment of the tubular bone,
    a first inner part, which is arranged displaceably in the axial direction inside the body and comprises a first fixation means for the fixation of a middle fragment of the tubular bone,
    a second inner part, which is arranged displaceably in the axial direction inside the body and comprises a second fixation means for the fixation of a second end fragment of the tubular bone, and
    a drive unit for the axial displacement of the first inner part relative to the second inner part,
    wherein the drive unit comprises an electric motor with a gearing, and
    wherein the electric motor and the gearing of the drive unit are integrated in one of the first inner part and the second inner part and are arranged inside the body between the first fixation means of the first inner part and the second fixation means of the second inner part,
    wherein the electric motor and the gearing are displaceable in the axial direction together with the one of the first inner part and the second inner part in which they are integrated.

2. The medullary pin according to claim 1, wherein the locking means is arranged in a first end region of the body.

3. The medullary pin according to claim 1, wherein the first inner part is arranged in a middle region of the body and/or the second inner part is arranged in a second end region of the body.

4. The medullary pin according to claim 3, wherein a first pair of axially extending oblong holes opposite each other is arranged in the middle region of the body and/or a second pair of axially extending oblong holes opposite each other is arranged in the second end region of the body.

5. The medullary pin according to claim 1, wherein a supply of energy to the drive unit occurs by way of an electrical connection, which is arranged inside the body.

6. The medullary pin according to claim 5, wherein the electrical connection is led through the second inner part.

7. The medullary pin according to claim 1, wherein the first fixation means of the first inner part has at least one through opening extending in a radial direction to accommodate a fixation bolt.

8. The medullary pin according to claim 1, wherein the second fixation means of the second inner part has at least one through opening oriented in a radial direction to accommodate each fixation bolt.

9. The medullary pin according to claim 1, wherein the first inner part and/or the second inner part have a cylindrical shape.

10. The medullary pin according to claim 1, wherein the locking means comprises boreholes and/or locking bolts which are oriented exclusively radially.

11. A medullary pin for a distraction with segment transport and subsequent lengthening of a tubular bone, wherein the medullary pin comprises:
    an at least partly hollow body extending in an axial direction of the medullary pin,
    a locking means for locking the body in a first end fragment of the tubular bone,
    a first inner part, which is arranged displaceably in the axial direction inside the body and comprises a first fixation means for the fixation of a middle fragment of the tubular bone,
    a second inner part, which is arranged displaceably in the axial direction inside the body and comprises a second fixation means for the fixation of a second end fragment of the tubular bone, and
    a magnetic drive unit for the axial displacement of the first inner part relative to the second inner part,
    wherein the drive unit comprises magnets inside the body, which are moved by a magnetic field generated outside the medullary pin, and
    wherein the magnets of the drive unit are integrated in one of the first inner part and the second inner part and are arranged inside the body between the first fixation means of the first inner part and the second fixation means of the second inner part, and
    wherein the magnets of the drive unit are displaceable in the axial direction together with the one of the first inner part and the second inner part in which they are integrated.

* * * * *